United States Patent [19]

Karás et al.

[11] Patent Number: 4,964,403
[45] Date of Patent: Oct. 23, 1990

[54] STABILIZER FOR THE TREATMENT OF THE FRACTURE OF THE NECK AND UPPER METAPHYSIS OF THE FEMUR

[75] Inventors: Wlodzimierz Karás, Dabrowa Górnicza; Robert Granowski; Witold Ramotowski, both of Warsaw; Aleksander Tuziemski, Sosnowiec; Jerzy Cieplak, Dabrowa Górnicza; Kazimierz Pilawski, Warsaw, all of Poland

[73] Assignee: Huta Baildon Przedsiebiorstwo Panstwowe Katowice, Zelazna, Poland

[21] Appl. No.: 132,937

[22] Filed: Dec. 15, 1987

[30] Foreign Application Priority Data

Dec. 19, 1986 [PL] Poland .................................. 263194
Dec. 19, 1986 [PL] Poland .................................... 78990

[51] Int. Cl.⁵ ............................ A61F 5/04; A61B 17/18
[52] U.S. Cl. ........................................ 606/60; 606/66; 606/73
[58] Field of Search ............ 623/16; 128/92 Z, 92 ZZ, 128/92 ZK, 92 ZW, 92 YV, 92 YP, 92 YG, 92 YF, 92 YE, 92 YL

[56] References Cited

U.S. PATENT DOCUMENTS

| | | | |
|---|---|---|---|
| 1,789,060 | 1/1931 | Weisenbach | 128/92 Z |
| 2,406,987 | 9/1946 | Anderson | 128/92 ZW |
| 2,699,774 | 1/1955 | Livingston | 128/92 YV |
| 3,094,120 | 6/1963 | Blosser | 128/92 YV |
| 3,554,193 | 1/1971 | Konstantinou et al. | 128/92 YV |
| 4,338,926 | 7/1982 | Kummer et al. | 128/92 YPX |
| 4,351,069 | 9/1982 | Ballintyn et al. | 128/92 YFX |
| 4,524,765 | 6/1985 | de Zbikowski | 128/92 YEX |
| 4,537,185 | 8/1985 | Stednitz | 128/92 YE |

FOREIGN PATENT DOCUMENTS

| | | | |
|---|---|---|---|
| 0013862 | 8/1980 | European Pat. Off. | 128/92 YP |
| 851028 | 9/1939 | France | 128/92 Z |
| 7346418 | 7/1975 | France | 128/92 YF |
| 2406430 | 6/1979 | France | 128/92 Z |
| 1487486 | 5/1987 | France | 128/92 ZZ |
| 475754 | 9/1969 | Switzerland | 128/92 YV |

OTHER PUBLICATIONS

"Rundloch-Winkelplatten", Osteo AG, p. 402, Selzach/Schweiz (1982).
"Stainless Steel for Hip Fixation", Zimmer, pp. c15 & c13, Great Britain (1975).
"OHS Kompressionshuftschraube", Osteo AG p. 2, Selzach/Schweiz (1982).
Parkhill's Clamp, Brickham's Operative Surgery, vol. 2, p. 364, 1924.

Primary Examiner—Richard J. Apley
Assistant Examiner—David J. Bender
Attorney, Agent, or Firm—Ladas & Parry

[57] ABSTRACT

A stabilizer for the treatment of the fractures of the neck and the upper metaphysis of the femur. The stabilizer plate 1 has a groove 2 in its bottom part and bent between tapered holes 3 passing into oval holes at their lower parts and tapered holes 4 passing into round holes at their lower part at an angle such that, after bone bolts 8 are secured in the porous bone fragments, the angle between them and plate 1 is approximately the same as that formed between the neck and shaft of the bone. The bolts 8 have a high pitch cortex thread 9 at the end of a cylindrical core, the latter having an enlarged part 12 on the opposite side and of the same width as that of groove 2 and terminating in a protruding shank 13 with a machine thread, while bolts 5 each have an enlarged disc-like part 7 disposed between the cortex and machine threads and having a width equal to that of groove 2, and conical-shaped nuts 14 are screwed on to protruding shanks 6 and 13.

3 Claims, 2 Drawing Sheets

STABILIZER FOR THE TREATMENT OF THE FRACTURE OF THE NECK AND UPPER METAPHYSIS OF THE FEMUR

CROSS-REFERENCE TO RELATED APPLICATIONS

Karas et al, U.S. Ser. No. 07/033,410 filed Apr. 1, 1987 is entitled "Drill Setting Guide for Drilling Holes in Bones", now U.S. Pat. No. 4,788,970 issued Dec. 6, 1988.

Karas et al, pending U.S. Ser. No. 07/038,053 filed Apr. 14, 1987 is entitled "Plates for Connecting Base Splinters with Bone Shafts" and discloses a preferred form of a bone screw or bolt and a specific nut configuration having a generally square upper cross sectional shape and a frusto-conical lower surface.

Karas et al, pending U.S. Ser. No. 07/133,059 filed Dec. 15, 1987 is entitled "Bone Bolt Nut Wrench", and discloses a tool specially adapted for application of a threaded bone screw or bone bolt and an associated bolt nut such that the single tool can be used to apply a bone screw or bolt as well as to apply and remove a threaded bone nut.

BACKGROUND OF THE INVENTION

1. Field of the Invention

The subject of this present invention is a stabiliser for the treatment of the fracture of the neck and upper metaphysis of the femur.

2. Description of the Prior Art

For the treatment of the fracture and fusion complications of the near base of the femur, use is made of angular plates, plate-nail sets and compression hip screws.

The angular plates are built up from an intra-osseous arm in the form of a wedge of various section and an external massive arm. A construction similar to the angular plate is shown by the plate-nail set. In the case of a uniform set the difference involves the external massive arm passing into a middle part in the form of a three-leaf nail. Split plate-nail sets consist of a three-leaf nail screwed to the plate. For the purpose of anastomosing fragments with the angular plate or the plate-nail set, the fragments should be initially locked in place by means of screws or wires. Next, a canal should be chiselled for the intra-osseous part of the plate or nail, drive the intra-osseous arm into the bone and bolt the external arm to the bone shaft.

The disadvantages of the anastomosis by the above-mentioned methods are that the external arm of the angular plate exerts undesired pressure on the bone. The very anastomosis of fractures involves wedging the intra-osseous arm in the fragment being attached, whereby the inter-fragment pressure developed by the implantate is very low.

The known compression hip bolts consist of a massive plate whose one end passes into a bush set at an angle of 135°-150° relative to the plate. A bone bolt is slid into the bush. The bone bolt is locked in place with a small additional metric screw. For the purpose of mounting the screw, it is necessary, among other things, to introduce a directional nail, to drill and tap a hole to screw in the bone bolt, to attach the plate to the bone shaft by means of the bone bolts, and finally, to compress the fragments with the metric screw. The disadvantage of the previously employed method is the disadvantageous pressure of the plate on the bone during the application of the compression hip bolts. Besides, the derotating action of the bolt depends on the magnitude of the compression of the fragments. The amount of the material introduced into the organism is too great and, thus, harmful.

For connecting bone fragments use is also made of bone compression anastomosis sets fulfilling the role of a stabiliser. They consist of a simple plate having round holes with a sliding surface inclined in the direction in which pressure is to be exerted, sets consisting of screws and end-threaded pins, heads and nuts.

The simple plate is fitted on the ends of the screw-pin sets complete with heads and tightened with the nuts. The ability to transmit varying loads by the plate stabiliser is mainly dependent on the reliability of the mechanical joints of the individual components. The previously employed nut has the form of a cylinder with its base shaped as a cone ensuring the strong mounting of the nut in the tapered hole of the plate.

A cross cut has been made in the top surface of the nut for the splines of the nut wrench. The disadvantage of the stabiliser of that type is that it is suitable only for the treatment of long bone fractures due to its construction. The screw-pin set consists of a smooth pin and a screw. The smooth pin does not allow any joint to be obtained with the bone when it is only slid into the hole made in a bone. Consequently, it is not possible to obtain an elastic deformation of the plate, which is required for compressing bone fragments. Thrust discs are individual parts and are applied on screw ends. They rest on the bone and exert pressure thereon, since the pins do not allow the plate to be lifted above the bone.

The force of tightening the nut on the threaded end of the bolt is small due to a low strength of the splines of the wrench. The latter should be accurately aligned with the bolt end since, otherwise, the splines get out of the cuts. Besides, the cuts grow over with tissue and, in order to unscrew the nut, it is necessary to remove the tissue from the cuts.

SUMMARY OF THE INVENTION

The stabiliser made according to this present invention has a plate, spongy bolts, bone bolts and nuts, the plate being bent at an angle of 120°-150°. The bottom part of the plate has a groove. One end of the plate has holes which are tapered at their upper part and oval at their lower part. The other end of the plate also has holes which are tapered at their upper part and oval at their lower part. The bone bolts have a cortex thread, with a protruding shank having a metric thread. Below the bone bolt shank there is a disc with a width equal to that of the groove. The end of the cylindrical core of the spongy bolts have a high cortex thread, with a protruding shank having a metric thread. Below the spongy bolt shank there is a disc having its width equal to that of the groove. In the front part of the spongy bolt there are cuts which extend around the tapered end and the first turns of the high cortex thread. The opposite end of the high cortex thread located adjacent the cylindrical core has a self-cutting point. On the shanks of the bone bolts and the spongy bolts extending through the plate there are nuts screwed thereon.

The nut for the metric thread has a cylindrical center part, a conical base and a square-shaped top part with truncated corners correspondingly to the diameter of the cylindrical part.

The stabiliser made according to this present invention shows a number of advantages. The plate of the stabiliser does not exert any harmful pressure on the bone and can be placed at any distance therefrom. This is attained thanks to the application of the discs being integral with the bolts and engaging the groove made in the bottom part of the plate, thereby lifting it above the bone and preventing the very bolt from unscrewing from the bone.

The spongy bolts have been tightened until the elasticity of the plate being deformed, which favourably affects the process of the bone fragments growing together. The cuts made at the beginning of the thread of the spongy bolts allow the bolts to be mounted in the head of the femur without previously tapping the holes with a tap.

The bolts having self-cutting points at the end of the cortex thread, they can be easily removed after the bone fracture has been healed. Besides, the amount of the metal introduced into an organism is considerably less than that by other methods. The nut screwed into the metric-threaded shank allows the application of a greater tightening force, only dependent upon the strength of the thread. The strength of the thread will increase for the same height of the nut. In addition to the above, the possibility of the wrench disengaging has been eliminated, even if the operator inclines it during tightening the nut. The shape of the nut allows the application of a wrench and removing the overgrown tissue surrounding the nut.

BRIEF DESCRIPTION OF THE DRAWINGS

The subject of this present invention is embodied in the drawing where.

DESCRIPTION OF THE PREFERRED EMBODIMENT

Figure 1:
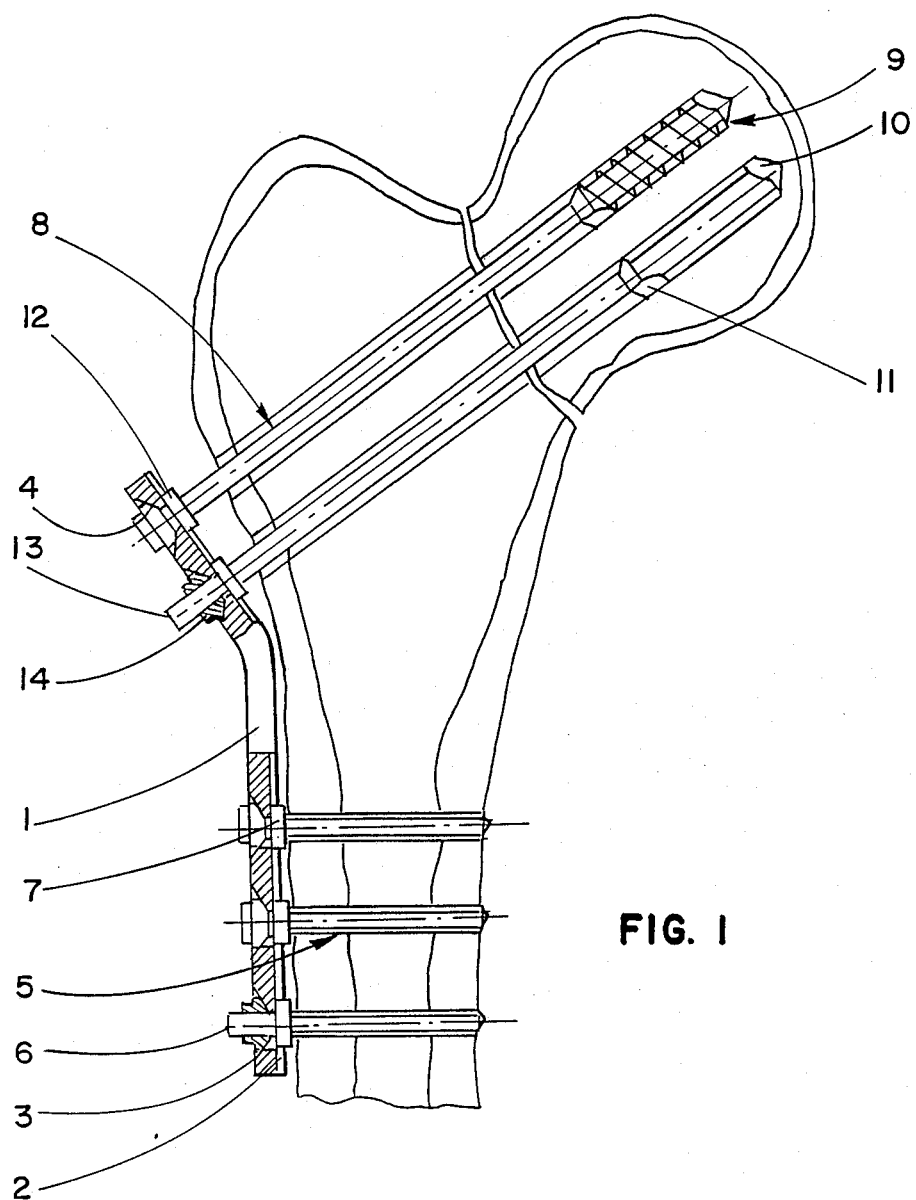
FIG. 1 shows a longitudinal section of the stabiliser together with the bone.
Figure 2:
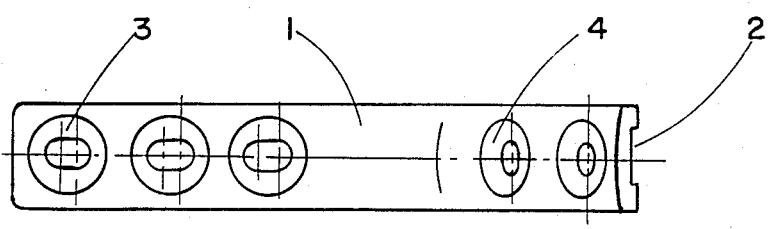
FIG. 2 shows a top view of the plate.
Figure 3:
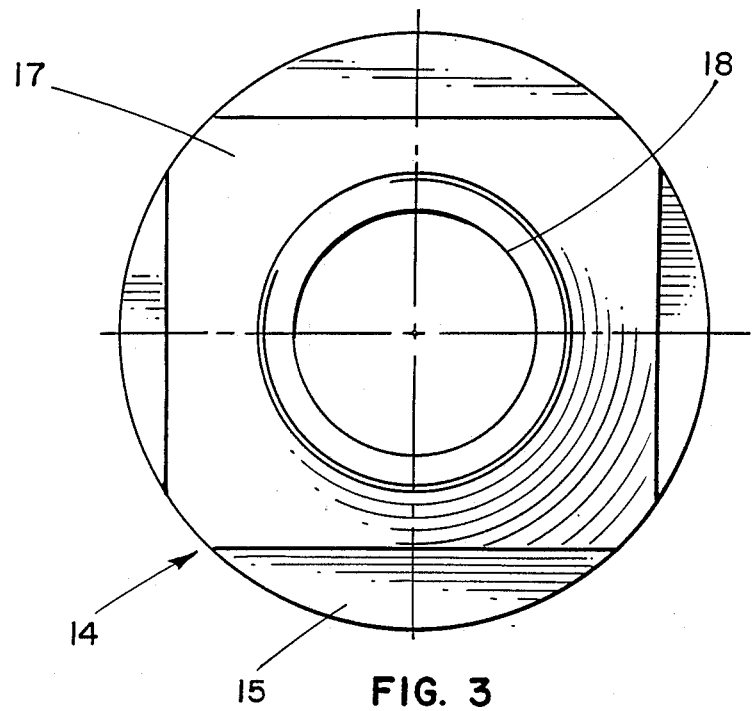
FIG. 3 a top view of the nut.
Figure 4:
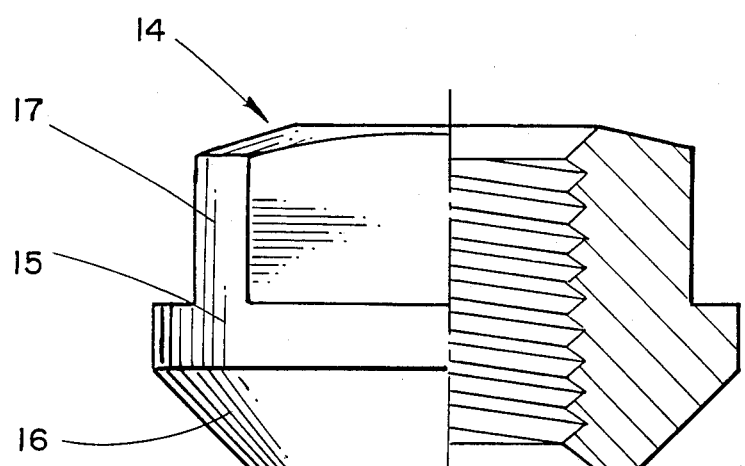
FIG. 4 a side half section of the nut.

Plate 1 bent at an angle of 120° and has groove 2 milled in its bottom part. Three holes 3 are made on the longer arm from the bend, said holes having a frusto-conical taper shape in their upper part and an oval shape in their lower part. Two holes 4 are made on the shorter arm from the side of the bend, said holes also having a frusto-conical taper shape in their upper part and a round shape in their lower part. Three bone bolts 5 have two kinds of thread, a cortex thread in the part to be screwed into the bone and a metric thread on shank 6. Below shank 6 there is a disc 7 of a width corresponding to that of groove 2. Two spongy screws 8 have high cortex thread 9 on the ends of the cylindrical core. In the front part of high cortex thread 9 cuts 10 are made which run around the taper and the first turns of high cortex thread 9.

A part of high cortex thread 9 has self-cutting point 11 at the side of the cylindrical core. The cylindrical core of spongy bolt 8 has disc 12 of a width such as that of groove 2 under shank 13 constituting its end. Shank 13 has a metric thread. Shanks 6 and 13 have nuts 14 screwed thereon. Nut 14 consists of cylindrical center part 15, conical base 16 and side surface 17. The latter is shaped as a square top part with truncated corners corresponding to the diameter of cylindrical part 15. In the middle of nut 14 is tapped hole 18.

In the case of a broken neck and upper metaphysis of the femur, the anastomosis of the fragment to the base of the femur takes place in the manner such that holes are first made in the base of the femur and in the fragment. Bone bolts 5 are introduced into the holes made in the base of the femur from the side of the cortex thread. On the other hand, spongy bolts 8 are introduced into the holes in the bone fragment from the side of the high cortex thread 9. Cuts 10 made at the beginning of high cortex thread 9 allow spongy bolt 8 to be fitted into the head of the femur without prior tapping the holes with a tap. Plate 1 is fitted onto protruding shanks 6 and 13 and discs 7 and 12 in the manner such that shanks 6 are in holes 3 and shanks 13 in holes 4.

With such a position of plate 1 on shanks 6 and 13, discs 7 and 12 are in groove 2. Nuts 14 are screwed onto shanks 6 and 13 protruding above plate 1. When nuts are being tightened, the base of the bone is moved up to the head of the femur due to the shape of holes 3 and 4 and, thanks to that, desired compression of the fragments is developed. Points 11 made on the ends of high cortex threads 9 cut the bone tissue when spongy bolts 8 are being screwed in, thanks to which they enable them to be easily removed from the bone on completion of the treatment of the fracture.

We claim:

1. A stabilizer for the treatment of fractures of a femur neck and the proximate upper metaphysis of the femur, comprising: an elongated bent plate having a planar base and an upper angularly disposed arm, the plate being adapted to be mounted by means of bone screws and fasteners adjacent the neck and proximate upper portion of a fractured femur, characterized in that the plate is provided with a first set of holes having on the side of the plate away from the bone a frusto-conical tapered shape, while on the side of the plate facing the bone an oval shape, and a second set of holes in the upper angular arm portion of the plate having on the side facing away from the bone a frusto-conical tapered shape and on the side adjacent the bone a circular shape, there being an elongated groove along the entire length of the plate on the side to face toward the bone, a first set of bone bolts adapted to be secured in the base of the femur in the upper proximate region near the fracture, said bolts having cortex-type high pitch threads for securing the same within the porous structure of the bone itself, there being a second set of elongated bolts adapted to be secured in the neck portion of the femur, said second set of bolts having cortex-type high pitch threaded portion at the leading ends thereof, and having an intermediate cylindrical unthreaded core adapted to pass through corresponding cylindrical holes pre-drilled in the neck portion of the femur and having at the remote outer ends, threaded shank portions adapted to be secured by means of fastener nuts to said plate arm, said second set of bolts having at least one cutting-edge extending around the lead end of said cortex thread part, to enable securing said bolts into the femur neck without pretapping holes in any bone fragments, both of said sets of bolts having second threaded shank portions at the remote head ends thereof in the form of a standard machine threads adapted to protrude outwardly through the sets of plate holes, said bolts further being provided with a disc in the form of an enlarged shoulder between the intermediate core and threaded outer shank, adapted to fit within said elongated groove in the plate upon assembly therewith, the remote threaded shank ends of said bolts extending through said sets of holes to be secured to the plate by means of corresponding sets of fastener nuts having internal threaded portions to match the threads on said protruding bolt shanks, and frusto-conical tapered base parts corresponding to the tapered holes in said plate, whereupon selective tightening of said fastener nuts over said stabilizer plate will enable deformation of said plate to apply appropriate tension forces to said elongated bone bolts without exertion of any adverse pressure by the plate against the bone.

2. A stabilizer according to claim 1, wherein said high pitch cortex thread portion on each of the second set of bone bolts adjacent said cylindrical core portion there is provided a self-cutting edge to facilitate removal.

3. A stabilizer according to claim 1, wherein the fastener nut has, in addition to said frusto-conical base part, a cylindrical center and a square-shaped top portion with truncated corners corresponding to the diameter of the cylindrical center part.

* * * * *